(12) United States Patent
McMullen

(10) Patent No.: US 6,379,848 B1
(45) Date of Patent: Apr. 30, 2002

(54) RETICLE FOR USE IN PHOTOLITHOGRAPHY AND METHODS FOR INSPECTING AND MAKING SAME

(75) Inventor: Thomas F. McMullen, San Antonio, TX (US)

(73) Assignee: Philips Electronics No. America Corp., New York, NY (US)

( * ) Notice: Subject to any disclaimer, the term of this patent is extended or adjusted under 35 U.S.C. 154(b) by 0 days.

(21) Appl. No.: 09/467,148

(22) Filed: Dec. 20, 1999

(51) Int. Cl.[7] .............................. G03F 9/00; G06K 9/00; G01B 11/24; G01B 11/14; G01B 11/26
(52) U.S. Cl. .............................. 430/5; 382/144; 348/87; 356/392; 356/396; 356/397
(58) Field of Search .............................. 430/5; 382/144; 348/87; 356/392, 396, 397

(56) References Cited

U.S. PATENT DOCUMENTS

| 5,475,766 | A | | 12/1995 | Tsuchiya et al. ............. 382/144 |
| 5,566,877 | A | | 10/1996 | McCormack ................. 228/105 |
| 5,804,340 | A | * | 9/1998 | Garza et al. .................... 430/5 |
| 6,106,980 | A | * | 8/2000 | Pierrat et al. ................... 430/5 |

FOREIGN PATENT DOCUMENTS

| DE | 43 07 590 A1 | 9/1994 |
| EP | 0 930 499 A1 | 7/1999 |

* cited by examiner

Primary Examiner—Janet Baxter
Assistant Examiner—Sin J. Lee
(74) Attorney, Agent, or Firm—Peter Zawilski

(57) ABSTRACT

A method for inspecting a reticle to evaluate the degree of corner rounding of a feature of a test pattern includes placing a reticle having a photomask formed thereon under a microscope. The photomask has a pattern corresponding to features of a semiconductor chip design defined therein. In addition, the photomask further has a test pattern and a crosshair orientation mark defined therein. The test pattern has at least one test corner for evaluating a degree of corner rounding when the test pattern is defined in the photomask. The crosshair orientation mark is defined in the photomask to orient a crosshair of the microscope relative to the test pattern. Once the crosshair of the microscope is aligned with the crosshair orientation mark, the crosshair of the microscope is used to evaluate the degree of rounding of the test corner of the test pattern. A method for inspecting a reticle to determine the pass/fail status of the reticle, a method for making a reticle, and a reticle for use in photolithography also are described.

12 Claims, 7 Drawing Sheets

RETICLE FOR USE IN PHOTOLITHOGRAPHY AND METHODS FOR INSPECTING AND MAKING SAME

BACKGROUND OF THE INVENTION

1. Field of the Invention

The present invention relates to semiconductor fabrication. More particularly, the invention relates to a method for inspecting a reticle for use in photolithography, a method for making a reticle for use in photolithography, and a reticle for use in photolithography.

2. Description of the Related Art

As is well known to those skilled in semiconductor fabrication, photolithography involves selectively exposing regions of a resist-coated silicon wafer to a radiation pattern, and developing the exposed resist to either protect or expose regions of underlying wafer layers (e.g., regions of substrate, polysilicon, or dielectric). In the fabrication of semiconductor chips, one of the problems experienced during photolithography is that the features defined in the wafer layer are subject to corner rounding. One source of this problem is the rounding of features that occurs during the manufacturing of the reticle, which includes the photomask in which a pattern corresponding to features at one layer of an integrated circuit (IC) design is defined.

FIG. 1A shows a conventional stepper apparatus 10 used in photolithography. Stepper apparatus 10 includes radiation source 12, reticle 14, and focusing lens 16. As shown in FIG. 1A, stepper apparatus 10 is disposed above resist-coated wafer 18, which is divided into a plurality of dies 20. In operation, radiation 22 (e.g., light) from radiation source 12 is projected onto the surface of resist-coated wafer 18. After passing through reticle 14 and focusing lens 16, radiation 22 contacts the surface of resist-coated wafer 18 within one of dies 20 and defines IC design pattern 24' in the die surface. This process is typically repeated until an IC design pattern has been defined in each of dies 20 by stepping stepper apparatus 10 in two dimensions above resist-coated wafer 18. Thereafter, conventional development, etching, and stripping operations are typically performed to define the features at one layer of the IC design.

FIG. 1B shows a detailed view of conventional reticle 14 shown in FIG. 1A. As shown in FIG. 1B, reticle 14 includes transparent glass plate 26 on which photomask 28 is formed. Photomask 28, which is formed of chromium or other suitable light-blocking material, has IC design pattern 24 defined therein. IC design pattern 24 corresponds to features at one layer in an IC design. When radiation 22 from radiation source 12 is directed toward reticle 14, radiation (e.g., light) passes through pattern 24, which corresponds to the portion of transparent glass plate 26 not covered by photomask 28, and projects onto resist-coated silicon wafer 18 (see FIG. 1A) disposed below the reticle.

Reticles are presently manufactured by depositing a chromium photomask on a transparent glass plate, coating the photomask with a resist, defining a pattern in the resist using a pattern generator, developing the resist, and subjecting the photomask to chemical processing to remove everything but the desired pattern from the glass plate. In the operation in which the pattern is defined in the resist, the pattern generator directs an electron beam to define the desired features in the resist.

FIG. 2A shows an exemplary ideal IC design pattern 24 that may be defined in a photomask. The ideal pattern 24 has well-defined outside corners 30 and inside corners 32. The corners 30 and 32 form sharp, 90 degree angles. Unfortunately, when the pattern is defined in the photomask, these corners are subject to rounding due to electromagnetic wave effects and chemical processing effects.

FIG. 2B illustrates the corner rounding that may occur during preparation of a photomask in which ideal IC design pattern 24 shown in FIG. 2A is to be defined. As shown in FIG. 2B, actual IC design pattern 24' has rounded outside corners 30a and rounded inside corners 32a. These corners do not form sharp, 90 degree angles and, consequently, the actual IC design pattern 24' does not have the desired shape of ideal IC design pattern 24. This is undesirable because the discrepancy in shape of desired features, e.g., metallization features, may render numerous devices on a wafer inoperable and thereby decrease the manufacturing yield.

The deleterious effects of corner rounding become more problematic at smaller feature sizes. Thus, as the feature sizes in modern IC designs continue to decrease, it becomes increasingly more important to monitor closely all potential sources of corner rounding to avoid excessive yield losses. As noted above, one source of corner rounding is the rounding of corners that occurs in the process of manufacturing the reticle.

To date, several approaches have been used to inspect reticles for corner rounding. In one approach, an optical inspection device is used to compare the actual features of the photomask to corresponding data on a data tape used to prepare the photomask. This approach is undesirable because it requires complex equipment that is not only expensive, but also may be difficult and time consuming to install and operate. In another approach, an operator inspects the reticles under a microscope to determine visually whether the degree of corner rounding of features defined in the photomask is acceptable. This approach suffers from the disadvantage that it may be inconsistent or unreliable because it relies upon the operator's subjective judgment to determine the acceptability of the reticle.

In view of the foregoing, there is a need for an inexpensive, consistent, and reliable method of inspecting reticles to determine whether the degree of corner rounding is within acceptable limits.

SUMMARY OF THE INVENTION

Broadly speaking, the present invention fills these needs by providing a photomask having a test pattern and a reference marker defined therein. When a reticle having the photomask formed thereon is inspected under a microscope, the crosshair of the microscope may be used in conjunction with the reference marker to evaluate the degree of corner rounding of a feature of the test pattern.

In one aspect of the invention, a method for inspecting a reticle to evaluate the degree of corner rounding of a feature of a test pattern is provided. In this method a reticle having a photomask formed thereon is placed under a microscope. The photomask has a pattern corresponding to features of a semiconductor chip design defined therein. In addition, the photomask further has a test pattern and a crosshair orientation mark defined therein. The test pattern has at least one test corner for evaluating a degree of corner rounding when the test pattern is defined in the photomask. The crosshair orientation mark is defined in the photomask to orient a crosshair of the microscope relative to the test pattern. Once the crosshair of the microscope is aligned with the crosshair orientation mark, the crosshair of the microscope is used to evaluate the degree of rounding of the test corner of the test pattern.

In another aspect of the invention, a method for inspecting a reticle to determine the pass/fail status of the reticle is provided. In this method, a reticle having a photomask formed thereon is placed under a microscope. The photomask has a pattern corresponding to features of a semiconductor chip design defined therein. The photomask further has a test pattern and a crosshair alignment mark defined therein. The test pattern has at least one test corner for determining a pass/fail status of the reticle. The crosshair alignment mark is defined in the photomask to orient a crosshair of the microscope relative to the test pattern. Once the crosshair of a microscope is aligned with the crosshair alignment mark, the crosshair of the microscope is used to determine the pass/fail status of the reticle.

In yet another aspect of the invention, a method for making a reticle is provided. In this method, a glass substrate is first provided. A photomask having a pattern corresponding to features of a semiconductor chip design is then generated. A cell that includes a test pattern and a reference marker is defined in the photomask. The reference marker is positioned relative to the test-pattern so that the reference marker can be used in conjunction with a crosshair of a microscope to inspect a feature of the test pattern. Finally, the photomask is formed on the glass substrate to provide a reticle.

In a still further aspect of the invention, a reticle for use in photolithography is provided. The reticle includes a glass substrate and a photomask formed on the glass substrate. The photomask has features of a semiconductor chip design, a test pattern, and a reference marker defined therein. The reference marker is positioned relative to the test pattern so that the reference marker can be used in conjunction with a crosshair of a microscope to inspect a feature of the test pattern.

The present invention advantageously provides a simple and inexpensive method for inspecting the features of a photomask formed on a reticle. The inspection methods of the present invention are reliable because they rely upon an objective standard for evaluating corner rounding of photomask features formed on a reticle. In addition, the present invention enables the uniformity of features formed at different locations on the reticle to be verified quickly and reliably.

It is to be understood that the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate exemplary embodiments of the invention and together with the description serve to explain the principles of the invention.

As shown in FIG. 1B, reticle 14 has a photomask formed thereon.

DETAILED DESCRIPTION OF THE INVENTION

Several exemplary embodiments of the invention will now be described in detail with reference to the accompanying drawings. FIGS. 1A, 1B, 2A, and 2B are discussed above in the "Background of the Invention" section.

Figure 1A:
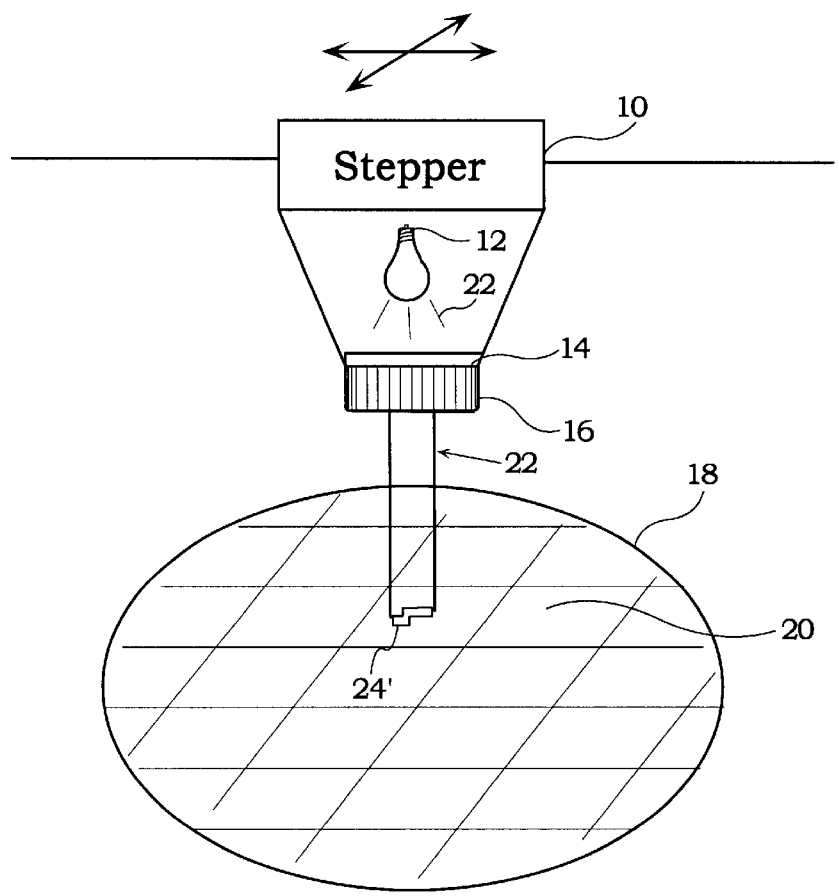
FIG. 1A shows a conventional stepper apparatus used in photolithography.
Figure 1B:
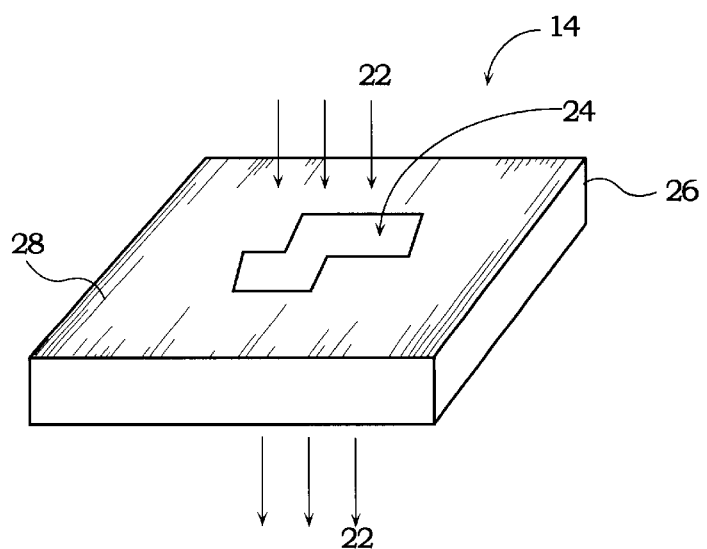
FIG. 1B shows a detailed view of reticle 14 shown in prior art FIG. 1A.
Figure 2A:
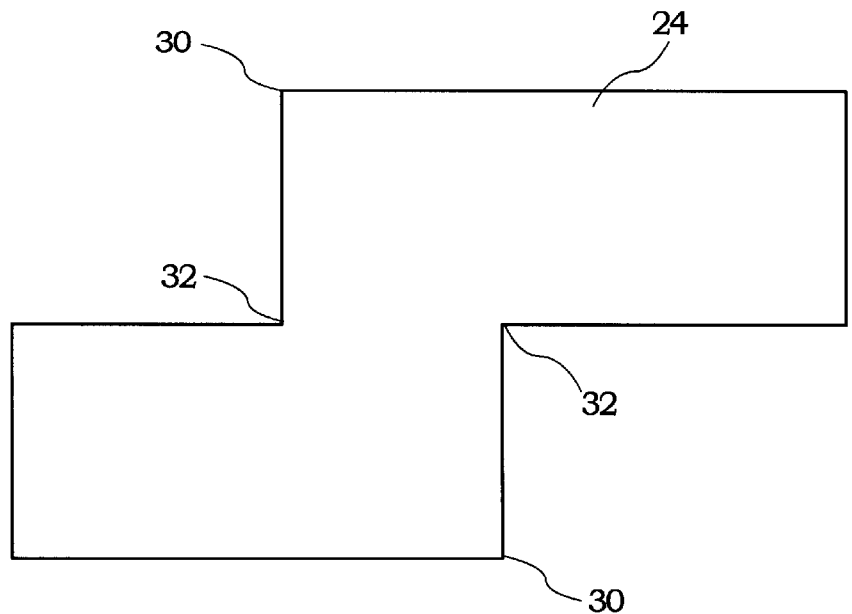
FIG. 2A shows an exemplary ideal IC design pattern that may be defined in a photomask.
Figure 2B:
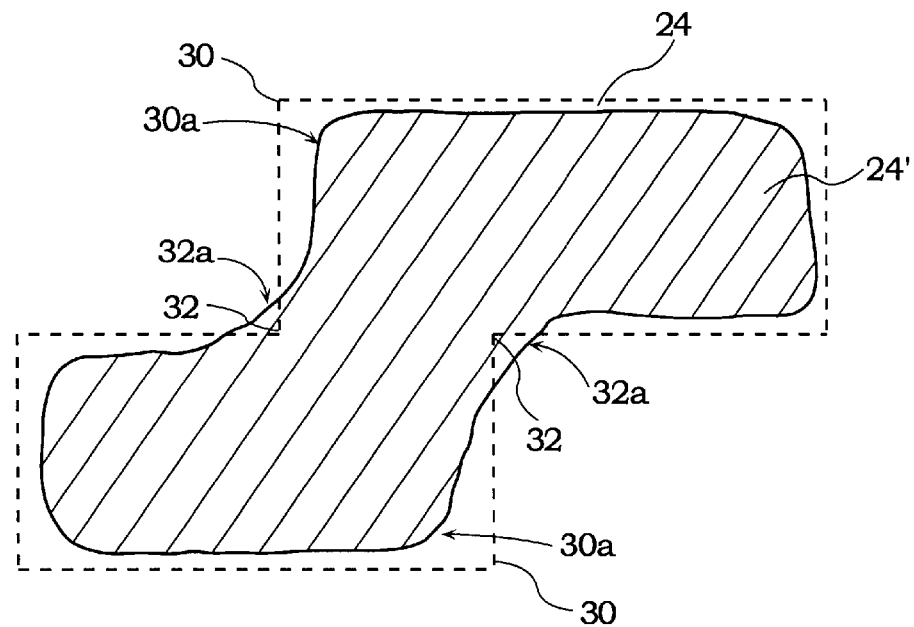
FIG. 2B illustrates the corner rounding that may occur during preparation of a photomask in which the ideal IC design pattern shown in FIG. 2A is to be defined.
Figure 3:
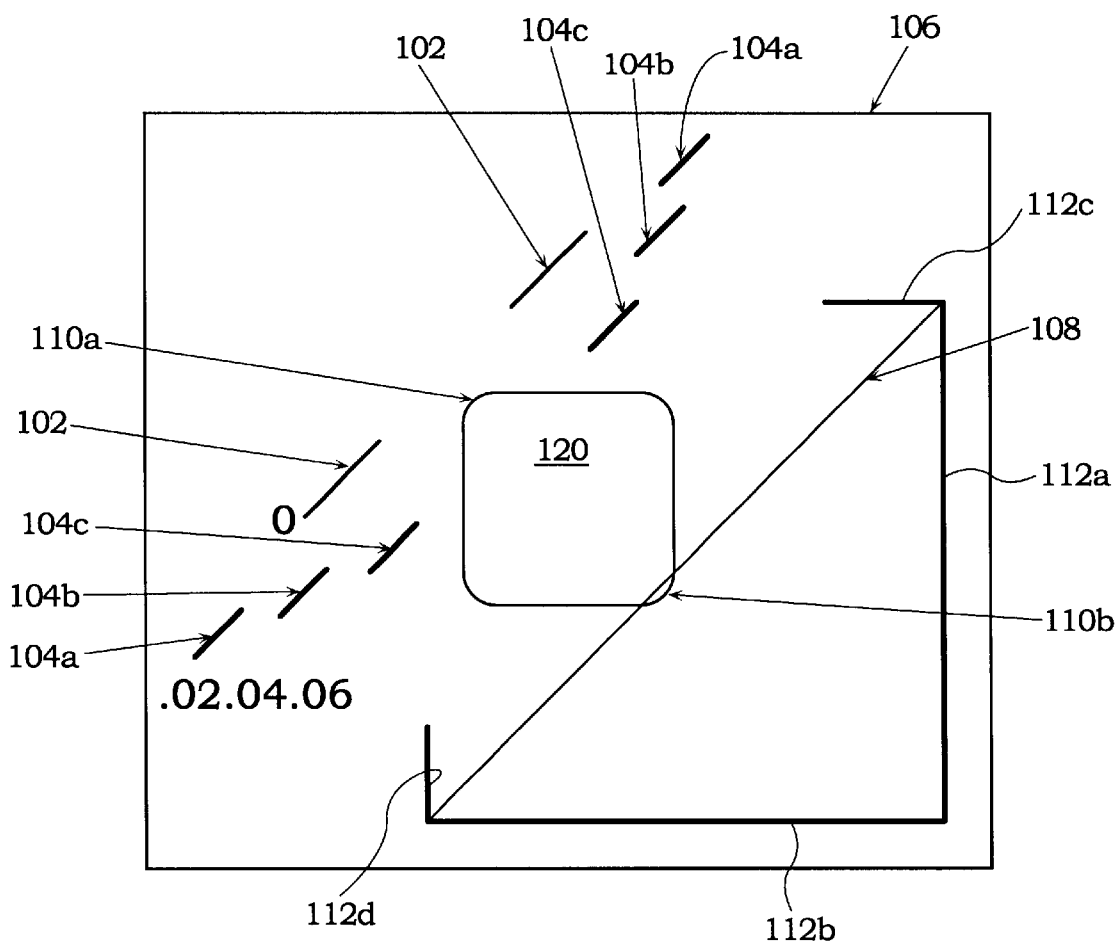
FIG. 3 shows a view taken through the lens of a microscope of a portion of a reticle in accordance with one embodiment of the present invention.

FIG. 3 shows a view taken through a microscope lens of a portion of a photomask in accordance with one embodiment of the present invention. As is well known to those skilled in the art, a photomask is formed on a reticle to enable a pattern corresponding to features at one layer in an integrated circuit (IC) design to be defined in the surface of a wafer. As shown in FIG. 3, the portion of photomask 106 has inspection features defined therein. The inspection features include a test pattern 120 and two sets of reference markers disposed proximate to test pattern 120 for enabling two methods for inspecting corner rounding.

The shape of test pattern 120 generally corresponds to features of a semiconductor design and, in one embodiment, has at least one test corner 110. By way of example, the features may correspond to corners of a metallization pattern. As shown in FIG. 3, test pattern 120 has a square shape with rounded corners 110. It will be apparent to those skilled in the art that the shape of the test pattern may be varied, provided the test pattern includes a representative corner corresponding to a feature in an integrated circuit design that can be inspected using the methods of the invention described herein.

The first set of reference markers may be used to measure the degree of corner rounding. As shown in FIG. 3, the first set of reference markers includes crosshair orientation marks 102 and corner rounding measurement marks 104a, 104b, and 104c. During inspection, the reticle is examined under a microscope and the relative distance between crosshair orientation mark 102 and the corner of test pattern 120 is determined using measurement marks 104, as will be described in more detail later.

As shown in FIG. 3, crosshair orientation mark 102 is oriented at about a 45 degree angle relative to a side of the test pattern; however, it will be apparent to those skilled in the art that this angle may be varied to suit the needs of particular situations. To enable the degree of corner rounding to be determined, crosshair orientation marks 102 are positioned relative to test pattern 120 such that a line defined by crosshair orientation marks 102 passes through a point defined by a hypothetical corner of test pattern having perfect right angles. As the result of the corner rounding that occurs during formation of the photomask, crosshair orientation marks 102 will be offset some distance from the rounded test corner 110a of test pattern 120 that is actually defined in photomask 106. As shown in FIG. 3, test corner 110a is the top left corner of test pattern 120. It will be apparent to those skilled in the art that the position of the test corner on the test pattern may be varied from that shown in FIG. 3.

The corner rounding measurement marks 104 may be used to measure the degree of corner rounding of the test corner of the test pattern. Each of measurement marks 104a, 104, and 104c is offset from crosshair orientation marks 102 to indicate a specific degree of corner rounding. If desired, the degree of corner rounding may be quantified. As shown in FIG. 3, the degree of corner rounding indicated by measurement marks 104a, 104b, and 104c is quantified as "0.02," ".04," and ".06," respectively. If desired, these numbers may indicate the finite distance between measurement marks 104 and crosshair orientation marks 102. Alternatively, these numbers may be arbitrarily selected to indicate a relative degree of corner rounding.

The second set of reference markers on photomask 106 may be used for determining whether the corner rounding is beyond the maximum level of acceptable corner rounding. In other words, the second set of reference markers may be used for determining whether the reticle should be rejected because of excessive corner rounding. As shown in FIG. 3, the second set of reference markers includes crosshair alignment marks 112a, 112b, 112c, and 112d. The crosshair orientation marks 112 define a first point and a second point that may be used to align the crosshair 108 of the microscope relative to test pattern 120 to indicate the maximum acceptable degree of corner rounding. Specifically, the intersection of marks 112a and 112c defines the first point and the intersection of marks 112b and 112d defines the second point. To determine the pass/fail status, i.e., the acceptability, of the reticle, crosshair 108 of the microscope is aligned such that it intersects the first and second points defined by the intersections of crosshair alignment marks 112. Once crosshair 108 is so aligned, the position of test corner 110b relative to crosshair 108 is used to determine the pass/fail status of the reticle. If the test corner 110b beyond crosshair 108, as shown in FIG. 3, then the reticle passes, i.e., is acceptable, because the degree of corner rounding is within the acceptable limit. On the other hand, if test corner 110b does not reach the crosshair 108, then the degree of corner rounding exceeds the acceptable limit and the reticle may be rejected.

As shown in FIG. 3, crosshair orientation marks 112 define a portion of a rectangle. Alternatively, crosshair orientation marks 112 may define other geometric shapes or elements, provided such marks allow the crosshair of the microscope to be appropriately positioned relative to the test pattern. For example, the crosshair orientation marks may include a first pair of intersecting line segments defining the first point and a second pair of intersecting line segments defining the second point. Similar to the embodiment shown in FIG. 3, the first and second points in this alternative embodiment should be positioned relative to the test corner so that the intersection of a line defined by the first and second points with the test corner defines a maximum amount of acceptable corner rounding.

Figure 4:
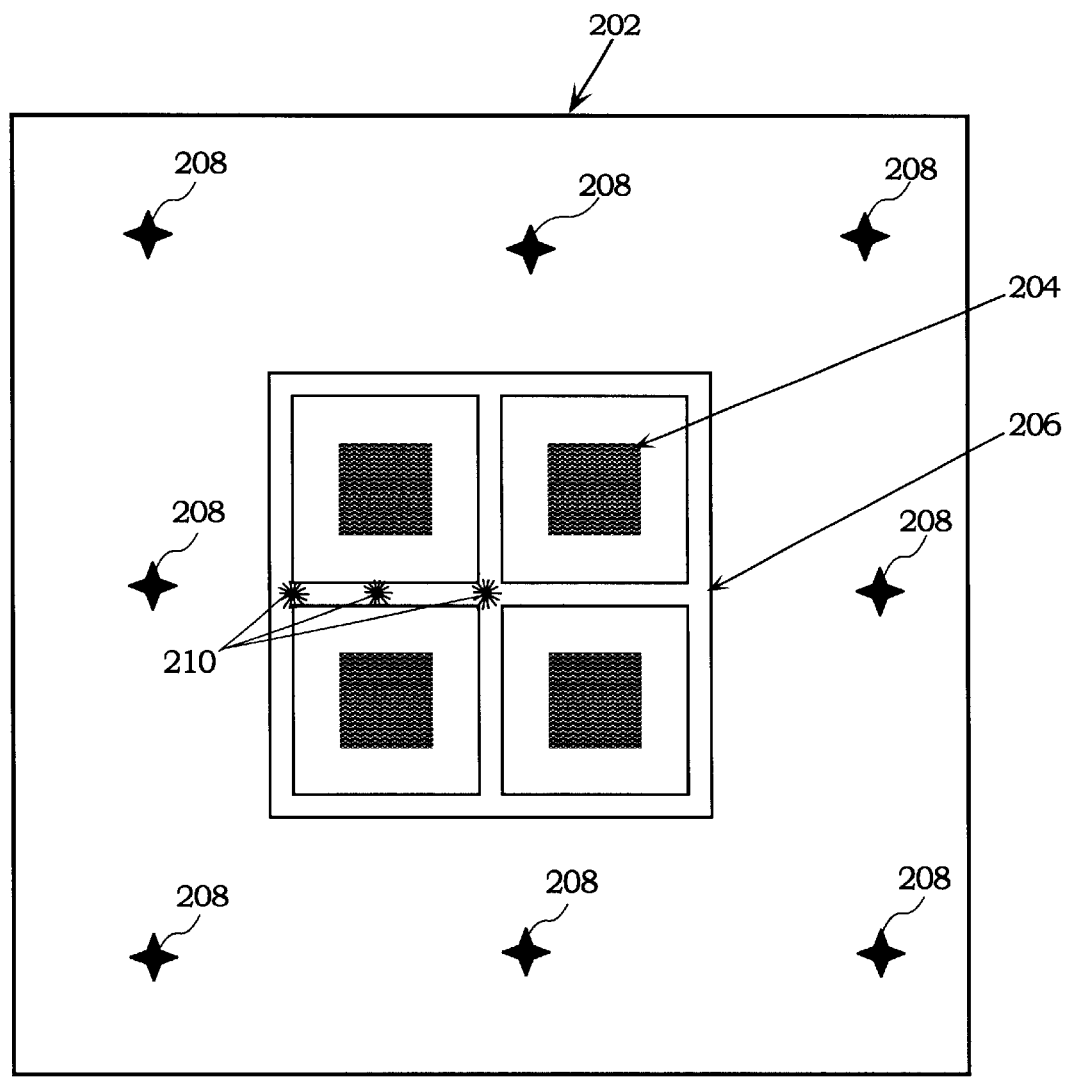
FIG. 4 shows the positioning of the inspection features on a reticle in accordance with one embodiment of the invention.

FIG. 4 shows the positioning of the inspection features on a reticle in accordance with one embodiment of the invention. As shown therein, reticle 202 has cells, which include the inspection features of the invention, defined in the photomask formed thereon at outer locations 208 and inner locations 210. In one embodiment, reticle 202 has four die portions 204 defined by scribe portions 206. As is well known to those skilled in the art, each die portion 204 corresponds to the portion of the wafer where active features for the semiconductor chip are fabricated. It will be apparent to those skilled in the art that the principles of the invention are applicable to reticles having any number of die portions 204 formed thereon.

As shown in FIG. 4, the cells at outer locations 208 are located outside of die portions 204 and scribe 206. The outer cells may be used to detect tilt or flatness defects resulting from manufacturing problems. The cells at inner locations 210 are located inside scribe 206, but outside of die portions 204. The inner cells may be used to detect radial processing defects resulting from manufacturing problems. The inner and outer cells may include one or both of the corner rounding measurement tools described above in connection with FIG. 3.

Figure 5:
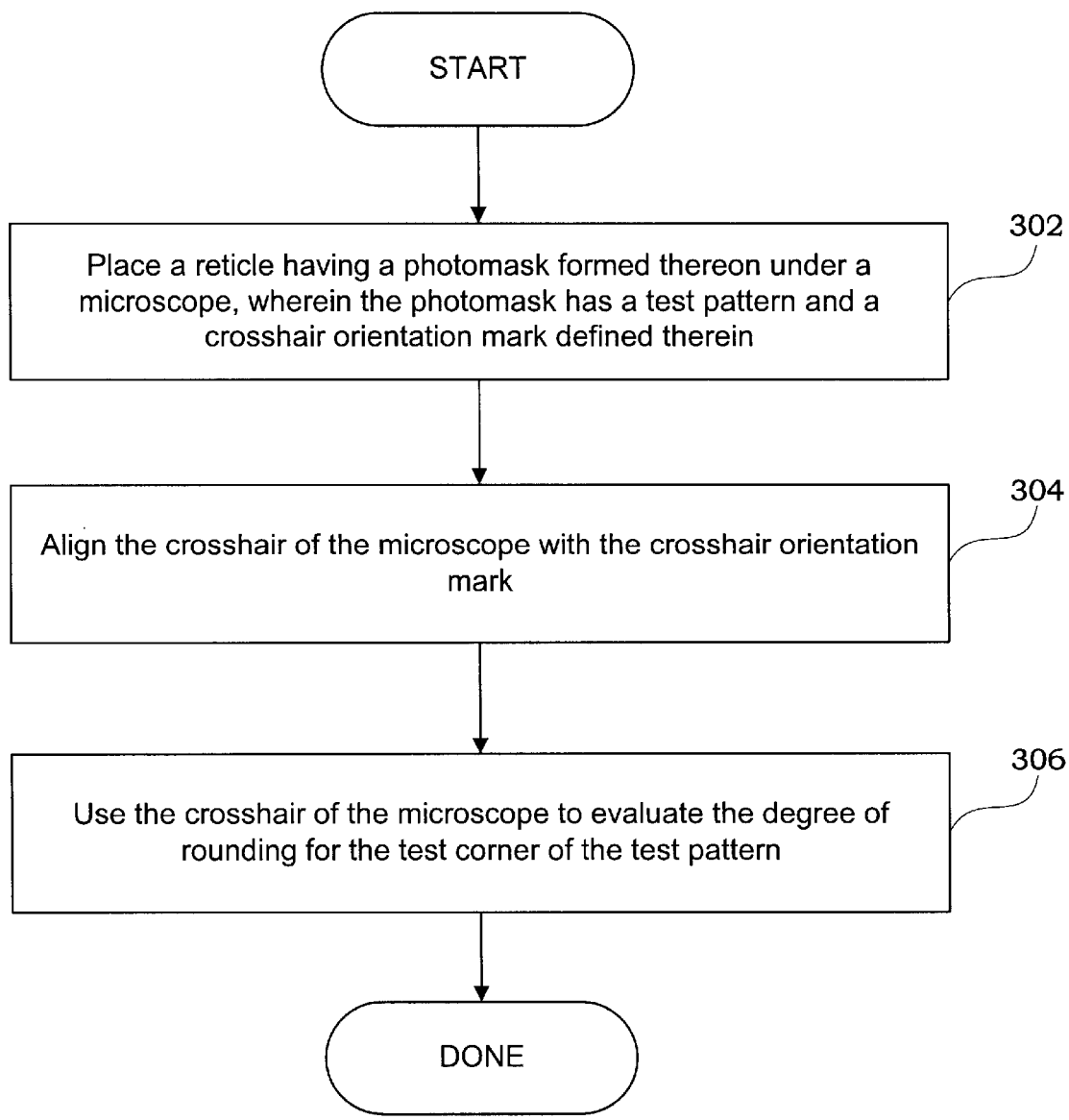
FIG. 5 is a flowchart illustrating the method operations performed in inspecting a reticle to evaluating the degree of rounding of features defined in a photomask in accordance with one embodiment of the present invention.

FIG. 5 is a flowchart illustrating the method operations performed in inspecting a reticle to evaluating the degree of rounding of features defined in a photomask in accordance with one embodiment of the present invention. The method begins in operation 302 in which a reticle having a photomask formed thereon is placed under a microscope. The photomask has a pattern corresponding to features of a semiconductor chip design defined therein. The photomask further has a test pattern and a crosshair orientation mark defined therein. In one embodiment, the photomask has the test pattern and the crosshair orientation marks shown in FIG. 3 defined therein. The test pattern has at least one test corner for evaluating a degree of corner rounding when the test pattern is defined in the photomask. The crosshair orientation mark is defined in the photomask so that the crosshair of the microscope may be oriented in a desired location relative to the test pattern.

Next, in operation 304, the crosshair of the microscope is aligned with the crosshair orientation mark. Once the crosshair is aligned with the crosshair orientation mark, the method proceeds to operation 306 in which the crosshair of the microscope is used to evaluate the degree of rounding for the test corner of the test pattern. The crosshair may be used to evaluate the degree of corner rounding by moving the stage of the microscope until the crosshair just touches the test corner of the test pattern defined in the photomask. The distance between the crosshair orientation mark and the crosshair of the microscope is indicative of the degree of corner rounding of the test corner of the test pattern. In one embodiment, a measurement scale such as, for example, corner rounding measurement marks 104 shown in FIG. 3, is defined in the photomask. This measurement scale may be used to obtain a value for the degree of corner rounding based on the position of the crosshair relative to the measurement scale.

Figure 6:
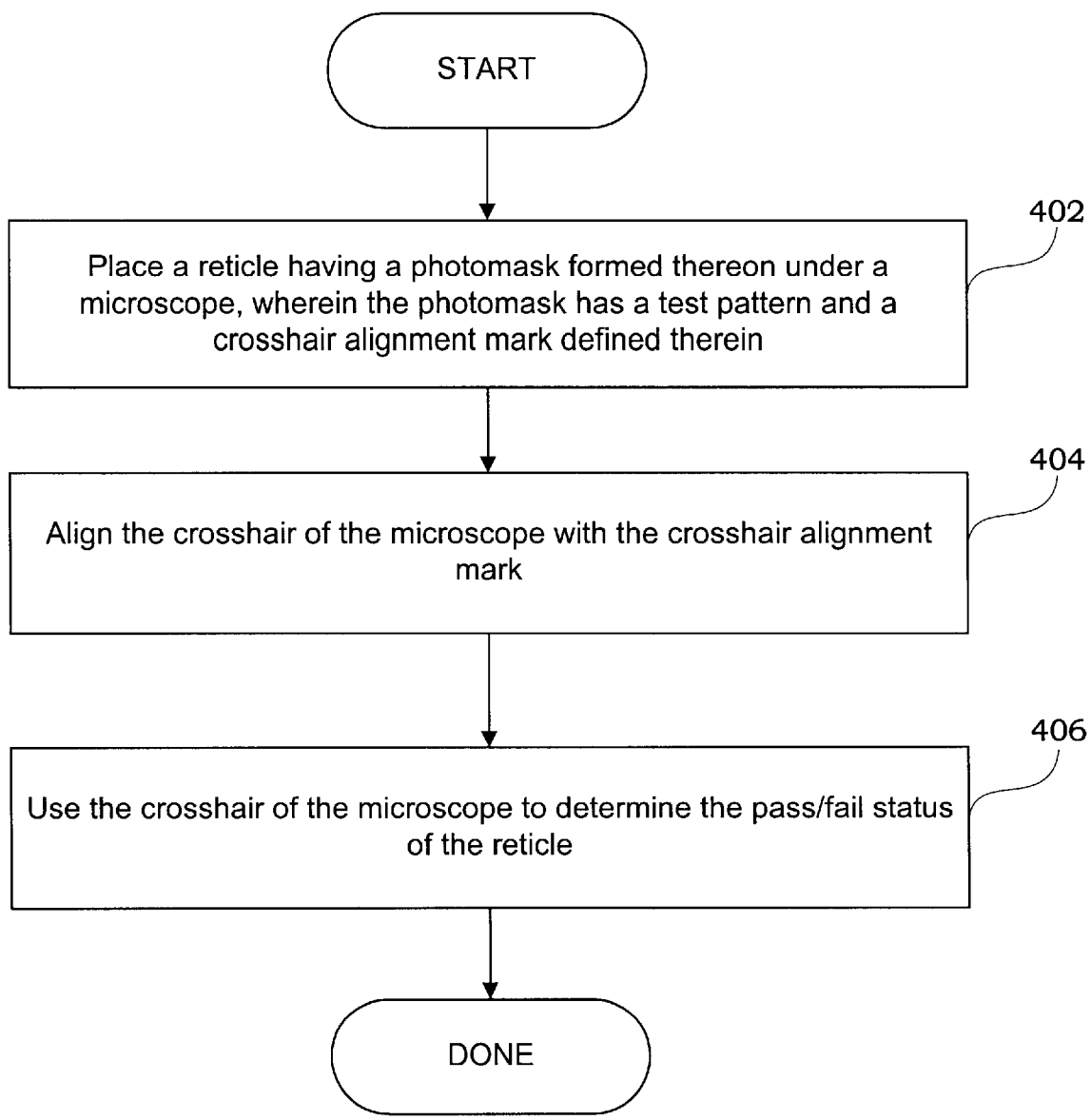
FIG. 6 is a flowchart illustrating the method operations performed in inspecting a reticle to determine the pass/fail status of the reticle in accordance with one embodiment of the present invention.

FIG. 6 is a flowchart illustrating the method operations performed in inspecting a reticle to determine the pass/fail status of the reticle in accordance with one embodiment of the present invention. The method starts in operation 402 in which a reticle having a photomask formed thereon is placed under a microscope. The photomask has a pattern corresponding to features of a semiconductor chip design defined therein. The photomask further has a test pattern and a crosshair alignment mark defined therein. The test pattern has at least one test corner for determining a pass/fail status of the reticle. The crosshair alignment mark is defined in the photomask to orient a crosshair of the microscope at a desired location relative to the test pattern.

Next, in operation 404, the crosshair of the microscope is aligned with the crosshair alignment mark. Once the crosshair of the microscope is aligned with the, crosshair alignment mark, the method proceeds to operation 406 in which the crosshair of the microscope is used to determine the pass/fail status of the reticle. As described above in connection with the description of FIG. 3, the position of the crosshair alignment, mark relative to the test pattern is selected such that the crosshair of the microscope defines the maximum acceptable amount of corner rounding when aligned with the crosshair alignment mark. If the test corner reaches or extends beyond the crosshair of the microscope, then the reticle passes, i.e., is acceptable. In other words, the degree of corner rounding in the test corner is within the maximum acceptable limit. If the test corner does not reach the crosshair of the microscope, then the reticle fails, i.e., is rejected. In other words, the degree of corner rounding in the test corner is beyond the maximum acceptable limit.

Figure 7:
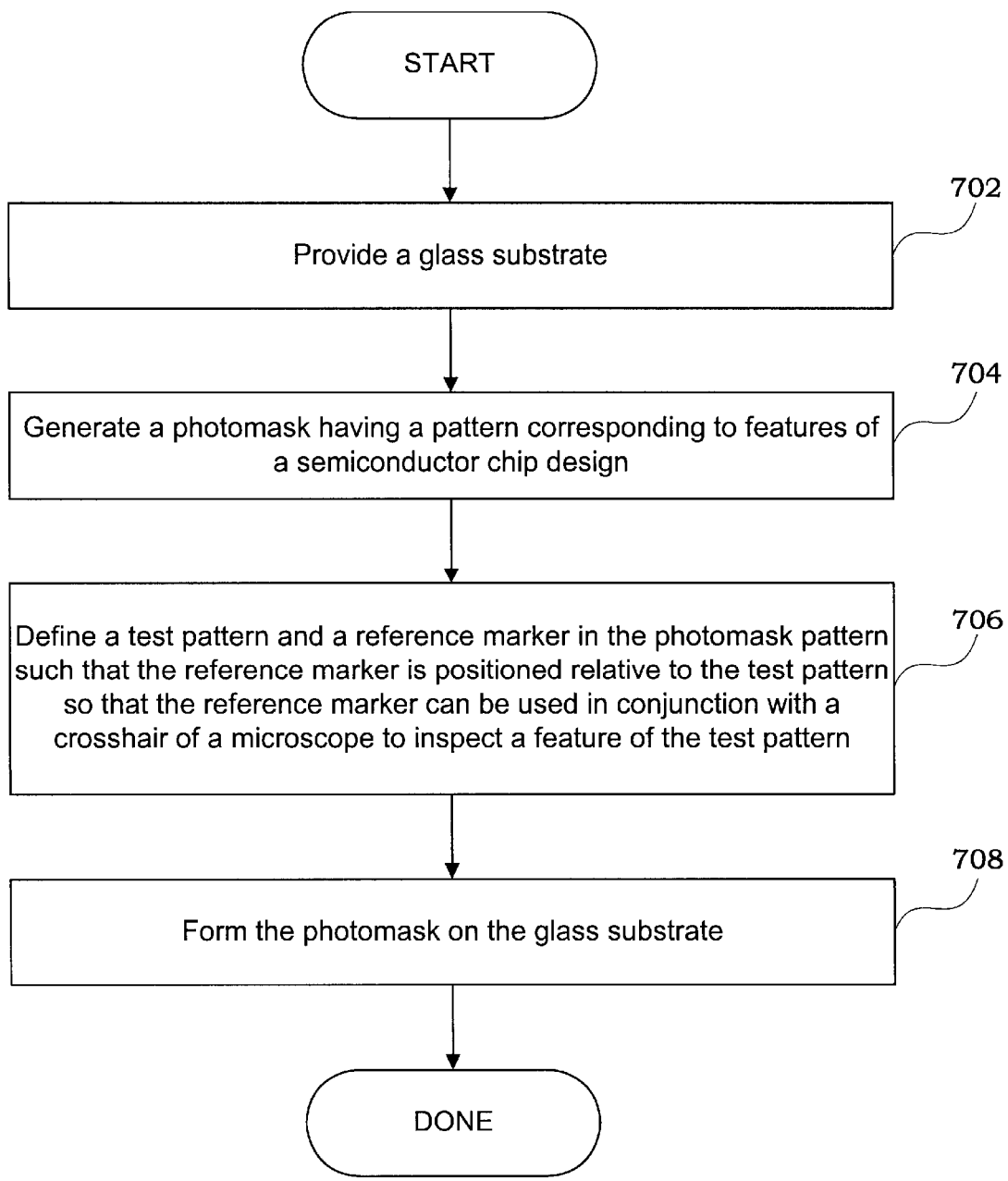
FIG. 7 is a flowchart illustrating the method operations performed in making a reticle in accordance with one embodiment of the present invention.

FIG. 7 is a flowchart illustrating the method operations performed in making a reticle in accordance with one embodiment of the present invention. The method starts in operation 702 in which a glass substrate is provided. In operation 704, a photomask having a pattern corresponding to features of a semiconductor chip design defined is generated. In one embodiment, the photomask pattern is generated by computer using suitable software. Next, in operation 706, a cell including a test pattern and a reference marker is defined in the photomask pattern. In one embodiment, the reference marker is positioned relative to the test pattern so that the reference marker can be used in conjunction with a crosshair of a microscope to inspect a feature of the test pattern. By way of example, the reference marker may be one or both of crosshair orientation mark 102 and crosshair alignment mark 112 shown in FIG. 3. The method then proceeds to operation 708 in which the photomask is formed on the glass substrate to provide a reticle. The photomask may be formed on the glass substrate using any suitable technique, e.g., the conventional technique described above.

If desired, a number of cells may be defined in the photomask pattern to detect tilt defects and radial processing defects of the photomask when formed on the glass substrate. In one embodiment, as shown in FIG. 4, a plurality of cells disposed at outer locations 208 are configured to detect tilt or flatness defects during manufacturing of the reticle. In addition, a plurality of cells disposed at inner locations 210 are configured to detect radial processing defects during manufacturing of the reticle.

In summary, the present invention provides a reticle for use in photolithography and methods for inspecting and making the reticle. The invention has been described herein in terms of several exemplary embodiments. Other embodiments of the invention will be apparent to those skilled in the art from consideration of the specification and practice of the invention. The embodiments and preferred features described above should be considered exemplary, with the invention being defined by the appended claims.

What is claimed is:

1. A method for making a reticle, the method comprising:
   providing a glass substrate;
   generating a photomask having a pattern corresponding to features of a semiconductor chip design;
   defining in the photomask a cell that includes a test pattern and a reference marker, the test pattern having at least one test corner for evaluating a degree of corner rounding when the test pattern is defined in the photomask or for determining a pass/fail status of the reticle, and the reference marker being positioned relative to the test pattern to orient a crosshair of a microscope to evaluate the degree of rounding of the test corner of the test pattern or to determine the pass/fail status of the reticle; and
   forming the photomask on the glass substrate.

2. The method of claim 1, further comprising defining the cell outside of a die portion and a scribe of the photomask.

3. The method of claim 2, further comprising configuring a plurality of cells to be used in conjunction with the microscope to detect tilt defects of the photomask.

4. The method of claim 1, further comprising defining the cell inside of a scribe of the photomask and outside of a die portion of the photomask.

5. The method of claim 4, further comprising configuring a plurality of cells to be used in conjunction with the microscope to detect radial processing defects of the photomask.

6. A reticle for use in photolithography, the reticle comprising:
   a glass substrate;
   a photomask formed on the glass substrate, the photomask having features of a semiconductor chip design, a test pattern, and a crosshair orientation mark defined therein, the test pattern having at least one test corner for evaluating a degree of corner rounding of the test pattern, and the crosshair orientation mark being positioned relative to the test pattern to orient a crosshair of a microscope to evaluate the degree of rounding of the test corner of the test pattern.

7. The reticle of claim 6, wherein the test pattern is a rectangle, the crosshair orientation mark is oriented at an approximately 45 degree angle relative to a side of the rectangle, and a line defined by the crosshair orientation mark passes through a point defined by the test corner of the rectangle in an absence of excessive corner rounding.

8. The reticle of claim 7, further comprising:
   a measurement scale defined in the photomask, wherein a value for the degree of corner rounding may be obtained based on a position of the crosshair relative to the measurement scale.

9. A reticle for use in photolithography, the reticle comprising:
   a glass substrate;
   a photomask formed on the glass substrate, the photomask having features of a semiconductor chip design, a test pattern, and a crosshair alignment mark defined therein, the test pattern having at least one test corner for determining a pass/fail status of the reticle, and the crosshair alignment mark being positioned relative to the test corner of the test pattern to orient a crosshair of a microscope to determine the pass/fail status of the reticle.

10. The reticle of claim 9, wherein the crosshair alignment mark includes a first pair of intersecting line segments defining a first point, and a second pair of intersecting line segments defining a second point, wherein the first and second points are positioned relative to the test corner so that an intersection of a line defined by the first and second points with the test corner defines a maximum acceptable amount of corner rounding.

11. A method for making a reticle, the method comprising:
    providing a glass substrate;
    generating a photomask having a pattern corresponding to features of a semiconductor chip design;
    defining in the photomask a cell that includes a test pattern and a reference marker, the cell being defined inside of a scribe of the photomask and outside of a die portion of the photomask, and the reference marker being positioned relative to the test pattern so that the reference marker can be used in conjunction with a crosshair of a microscope to inspect a feature of the test pattern; and
    forming the photomask on the glass substrate.

12. The method of claim 11, further comprising configuring a plurality of cells to be used in conjunction with the microscope to detect radial processing defects of the photomask.

* * * * *